(12) United States Patent
Turnquist et al.

(10) Patent No.: US 8,939,913 B2
(45) Date of Patent: Jan. 27, 2015

(54) MONITORING SYSTEM

(75) Inventors: Douglas G. Turnquist, Salt Lake City, UT (US); Brent W. Snow, Salt Lake City, UT (US); Philip Eggers, Salt Lake City, UT (US)

(73) Assignee: Thermimage, Inc., Salt Lake City, UT (US)

( * ) Notice: Subject to any disclaimer, the term of this patent is extended or adjusted under 35 U.S.C. 154(b) by 1084 days.

(21) Appl. No.: 12/713,099

(22) Filed: Feb. 25, 2010

(65) Prior Publication Data

US 2010/0222776 A1 Sep. 2, 2010

Related U.S. Application Data

(60) Provisional application No. 61/156,444, filed on Feb. 27, 2009, provisional application No. 61/156,441, filed on Feb. 27, 2009, provisional application No. 61/156,438, filed on Feb. 27, 2009, provisional application No. 61/156,433, filed on Feb. 27, 2009, provisional application No. 61/156,427, filed on Feb. 27, 2009, provisional application No. 61/156,407, filed on Feb. 27, 2009, provisional application No. 61/156,401, filed on Feb. 27, 2009, provisional application No. 61/156,393, filed on Feb. 27, 2009, provisional application No. 61/156,382, filed on Feb. 27, 2009.

(51) Int. Cl.
*A61B 5/00* (2006.01)
*A61B 5/01* (2006.01)
*A61B 18/18* (2006.01)
*A61B 18/00* (2006.01)
*A61G 15/10* (2006.01)

(52) U.S. Cl.
CPC .................. *A61B 5/01* (2013.01); *A61B 5/6804* (2013.01); *A61B 5/6887* (2013.01); *A61B 18/18* (2013.01); *A61B 18/1815* (2013.01); *A61B 5/4547* (2013.01); *A61B 2018/00023* (2013.01); *A61G 15/10* (2013.01)
USPC ........................................................ 600/549

(58) Field of Classification Search
USPC ................... 600/549, 587, 595; 374/158, 163
See application file for complete search history.

(56) References Cited

U.S. PATENT DOCUMENTS

| | | |
|---|---|---|
| 3,581,570 A | 6/1971 | Wortz |
| 4,140,130 A | 2/1979 | Storm, III |

(Continued)

FOREIGN PATENT DOCUMENTS

| | | |
|---|---|---|
| JP | 04-073908 | 6/1992 |
| JP | 05-293086 | 11/1993 |

(Continued)

OTHER PUBLICATIONS

International Preliminary Report on Patentability from related PCT Patent Application No. PCT/US2010/025550, Jun. 1, 2011.

(Continued)

*Primary Examiner* — Adam Eiseman
(74) *Attorney, Agent, or Firm* — Phillips Ryther & Winchester; Matthew D. Thayne (57) ABSTRACT

A heating and monitoring system is described having a focused antenna to monitor temperature of internal tissue and or bodily fluids in a non-invasive way. The focused antenna is shielded to form and relatively small and manageable package that can be placed to monitor internal tissue and/or bodily fluids.

20 Claims, 6 Drawing Sheets

(56) References Cited

U.S. PATENT DOCUMENTS

| | | | |
|---|---|---|---|
| 4,435,092 A * | 3/1984 | Iuchi | 374/129 |
| 4,513,750 A | 4/1985 | Heyman et al. | |
| 4,557,272 A | 12/1985 | Carr | |
| 4,605,012 A | 8/1986 | Ringeisen et al. | |
| 4,647,281 A | 3/1987 | Carr | |
| 4,798,215 A | 1/1989 | Turner | |
| 5,255,979 A * | 10/1993 | Ferrari | 374/158 |
| 5,275,594 A | 1/1994 | Baker et al. | |
| 5,370,121 A | 12/1994 | Reichenberger et al. | |
| 5,496,271 A | 3/1996 | Burton et al. | |
| 5,503,150 A | 4/1996 | Evans | |
| 5,542,915 A | 8/1996 | Edwards et al. | |
| 5,628,771 A | 5/1997 | Mizukawa et al. | |
| 5,660,836 A | 8/1997 | Knowlton | |
| 5,685,839 A | 11/1997 | Edwards et al. | |
| 5,797,398 A | 8/1998 | Bowman | |
| 5,833,625 A | 11/1998 | Essen-Moller | |
| 5,913,886 A | 6/1999 | Soloman | |
| 5,935,075 A | 8/1999 | Casscells et al. | |
| 5,954,668 A | 9/1999 | Uber et al. | |
| 6,181,970 B1 | 1/2001 | Kasevich | |
| 6,245,094 B1 | 6/2001 | Pompei | |
| 6,329,655 B1 * | 12/2001 | Jack et al. | 250/338.1 |
| 6,330,479 B1 | 12/2001 | Stauffer | |
| 6,347,251 B1 | 2/2002 | Deng | |
| 6,475,159 B1 | 11/2002 | Casscells et al. | |
| 6,615,071 B1 | 9/2003 | Casscells | |
| 6,773,159 B2 | 8/2004 | Kim et al. | |
| 7,217,245 B1 | 5/2007 | Snow et al. | |
| 7,263,398 B2 | 8/2007 | Carr | |
| 7,354,195 B2 * | 4/2008 | Sakano | 374/208 |
| 2002/0126731 A1 | 9/2002 | Stergiopoulos et al. | |
| 2002/0183621 A1 | 12/2002 | Pfeiffer et al. | |
| 2003/0130575 A1 | 7/2003 | Desai | |
| 2004/0215098 A1 * | 10/2004 | Barton et al. | 600/549 |
| 2004/0249272 A1 | 12/2004 | Carr | |
| 2005/0245839 A1 * | 11/2005 | Stivoric et al. | 600/549 |
| 2005/0267382 A1 * | 12/2005 | Church et al. | 600/549 |
| 2007/0196282 A1 | 8/2007 | Oliver | |
| 2009/0012417 A1 | 1/2009 | Carr | |
| 2009/0275808 A1 * | 11/2009 | DiMaio et al. | 600/301 |
| 2010/0069782 A1 | 3/2010 | Icove et al. | |
| 2011/0051776 A1 * | 3/2011 | Bieberich et al. | 374/163 |

FOREIGN PATENT DOCUMENTS

| | | |
|---|---|---|
| JP | 2008-099996 | 5/2008 |
| WO | WO 00-07665 | 7/2002 |
| WO | WO 2005-112179 | 12/2007 |

OTHER PUBLICATIONS

PCT Search Report from related case, Oct. 12, 2010.

* cited by examiner

MONITORING SYSTEM

RELATED APPLICATIONS

This application claims benefit and priority from U.S. Provisional Patent Application Nos. 61/156,444, 61/156,441, 61/156,438, 61/156,433, 61/156,427, 61/156,407, 61/156,401, 61/156,393, 61/156,382, each filed on Feb. 27, 2009, and each of which is incorporated herein by reference in its entirety.

This application is part of a group of similar applications including U.S. patent application Ser. No. 12/713,057, filed Feb. 25, 2010, U.S. patent application Ser. No. 12/713,079 filed Feb. 25, 2010, U.S. patent application Ser. No. 12/713,099, filed Feb. 25, 2010, and U.S. patent application Ser. No. 12/713,114 filed Feb. 25, 2010.

FIELD

This application relates generally to noninvasive thermal therapy and diagnostic devices and methods. More specifically, the present invention relates to devices and methods to non-invasively heat bodily tissues and fluid using emitted energy and non-invasively measure the resulting temperature changes in the target and surrounding fluid and tissue to detect and/or treat for various physical conditions, such as, for example, vesicoureteral reflux.

BACKGROUND

There are numerous diseases which can be treated successfully if detected early, but which can cause long term damage if not timely diagnosed and treated. Diseases such as vesicoureteral reflux can cause significant harm to an individual, but are not easily diagnosed without invasive procedures.

In vesicoureteral reflux bladder urine flows back up into the ureters and into the kidneys. The urine can cause kidney infections which can be painful. Moreover, repeated infections can cause long term kidney damage. While vesicoureteral reflux can be treated with medication or by surgical techniques, vesicoureteral reflux is difficult to properly diagnose.

Approximately 2% of all children at any one time have a urinary tract infection. When a child has had more than one kidney infection, it is desirable to determine if the child has vesicoureteral reflux. Two radiologic imaging studies are commonly utilized: voiding cystourethogram (VCUG) and a nuclear cystogram. A VCUG is performed in humans of all ages by first placing a sterile catheter in the patient's urethra and through the catheter instilling radiopaque contrast, such as Cystografin. The kidneys and bladder are observed during a bladder filling and emptying cycle using x-rays. The patient has an initial x-ray film taken, then an anterior-posterior film and then films in each lateral oblique. When voiding is initiated, fluoroscopy is utilized, and spot films are taken to document changes during voiding. This process has been necessary to evaluate bladder anatomy, function, elimination and confirm the existence of vesicoureteral reflux. After the first infection it is currently recommended that patients undergo a VCUG and a renal imaging study. However, doctors are sometimes reluctant to order the invasive VCUG until other infections occur. Of the VCUGs performed, approximately one of three patients will have vesicoureteral reflux. The reflux is graded and treatment is assigned on the basis of severity. About three-quarters of the patients are assigned to medical management and are screened with a VCUG each year until their reflux resolves. This averages about three years of waiting before resolution occurs. Patients who undergo surgical correction of their reflux also require a follow-up VCUG to evaluate the success of the procedure. Patients with enuresis either at night or during the day are evaluated with VCUGs on occasion. Since the test is currently invasive it is withheld until the patients are older or unusual symptoms indicate its necessity. It will be appreciated that the VCUG procedure is uncomfortable and can be traumatic, particularly for children.

Likewise, various other conditions exist in which body fluids, such as urine or blood, improperly flow as a result of disease or dysfunction. For example, gastroesophageal reflux is common in young children. Other conditions involve disruptions in blood flow or myocardial function resulting from narrowing of the aorta, blood clots, or malfunction of the enterohepatic circulation or a portion of this system, e.g. the intestine, liver or gall bladder, or disruptions in flow of cerebrospinal fluid. Diagnosis of such conditions has often required invasive procedures such as use of catheters or tubes.

Besides the diseases above, body tissues are subject to other abnormalities including cancer, scarring, inflammation and reduced function. One potential effect of the abnormalities includes abnormal tissue abnormally encouraging or restricting thermal spread. Thus, the improper flow of bodily fluids may be a condition that should be treated, or may be a symptom of a disease in need of treatment. Either way, prompt detection of such conditions would be beneficial.

There has been some discussion regarding administering microwave or ultrasound energy through an external energy source to warm a fluid in a target organ or tissue and detecting a warmed fluid distant from the target. (See e.g. U.S. Pat. No. 7,217,245). However, blind application of the thermal energy for a predetermined time may cause many problems, such as mis-targeting of the device, over or under heating of the target area, skin burns by mis-placement of the device and/or uncomfortable or damaging heating of the antenna itself against the patient.

There has also been discussion about a flexible microwave antenna array on a flexible circuit board. (See e.g. U.S. Pat. No. 6,330,479). However, sensing deep tissue temperature in a non-invasive manner can be difficult, as the emitted energy is small.

As diseases such as vesicoureteral reflux have relied on invasive and traumatic diagnosis procedures, a non-invasive and less traumatic diagnosis method and equipment would be desired. Moreover, a method for diagnosing or treating diseases with thermal energy which does not burn or otherwise discomfort patients would also be desirable.

SUMMARY

Embodiments of improved noninvasive heating and monitoring devices and methods of use are disclosed below. According to some embodiments, one or more microwave antennas are directed at a target organ or tissue, such as the bladder. Signals broadcast by the antenna(s) are used to heat liquid within the targeted tissue or organ (e.g. the bladder, gall bladder, etc.). A temperature sensing device, such as a radiometer, may be directed at the target organ or tissue and its temperature monitored to determine the extent to which heating has occurred at the desired location. The temperature sensing device or a second temperature sensing device may then be directed at a secondary location to detect an abnormal rise (or abnormal lack of rise) in temperature. If the temperature sensed at the secondary location is other than what would be expected in a healthy individual, a reading can be taken which is indicative of a disease or dysfunction. While discussed principally in the context of urine, other body fluids such as blood, bile, cerebrospinal fluid, lymph or other gastric fluids could also be used to diagnose abnormal physical conditions. Similarly, the target organ or tissue may be monitored for an abnormal dissipation of heat as evidence of disease/dysfunction.

In some embodiments, a heating and monitoring device includes an array of microwave elements that direct energy to a focal point or area. These microwave elements may be controlled separately or as a single entity Likewise, the microwave elements can be used simultaneously or alternatingly to obtain desired heating characteristics.

The microwave elements may be alternately activated such that the focal point is subject to a more consistent thermal energy from alternating microwave elements. However, by alternating the microwave elements, the tissue between the microwave elements and the focal point is subject to only the energy of a single microwave element and less frequently than the focal point. Thus the intervening tissue may maintain a lower temperature, while the focal point may be heated to a desired temperature. This may reduce and hopefully eliminate discomfort or burns to the surface tissue or intervening tissues, while providing enough energy to heat the focal point to obtain the desired temperature.

Some embodiments of the present invention provide for a noninvasive method for determining the condition of tissues by administering external energy with an array device to heat a tissue while measuring the temperature changes and heat dissipation of the tissue and comparing to measurements of temperature changes in normal tissues when heated. For example, in some embodiments, an array of microwave elements may include one or more passive elements or sensors that may be used to monitor the temperature of the surface area of the tissue. If the tissues at the surface approach a threshold, the sensors can signal an alarm or may alter the application of energy from the microwave elements. This ensures that the surface temperature does not exceed desired limits and prevents burning or causing discomfort in the individual.

In some embodiments, temperature monitors, may be further enabled or enhanced to enable more accurate deep tissue readings. The device may be configured, for example, to disable the active elements (i.e. energy applying elements such as microwave antennas) to reduce any noise produced by the active elements. A passive element or sensor may then take readings between application of energy from the active elements to obtain a more accurate temperature measurement due to a decrease in background noise or signals.

The monitors may also be directionally shielded such that the sensor may have increased sensitivity at the desired anatomy, and minimized sensitivity to radiated heat from other tissues. The increased sensitivity and decreased noise may be especially important for deep-tissue or organ observation as the received signal may be as small as −160 dBm.

In some embodiments, the surface area around the microwave elements may be cooled. In some embodiments, the microwave elements may be covered with passive cooling mechanisms such as water or gel (i.e. a heat sink), to reduce the risk of burns caused by the microwaves. Alternatively, active cooling mechanisms, such as a heat pump, a heat pipe, recirculator, a refrigerated coil, etc., or any other cooling mechanism can be used to keep tissues near the surface cool while deeper tissues are heated.

In other embodiments, monitoring the surface temperature may be used to control how the microwave elements are powered or which of the array elements are active at any particular time. By modulating the power or by selectively activating different elements in the array, the surface temperature and the internal energy deposition at any point may be kept low while still heating the internal target area.

The focal area or another area may be monitored for temperature difference after heating by a detecting mechanism such as an antenna disposed in communication with a radiometer. Heat dissipation from the focal area different from normal or control tissue may indicate disease or dysfunction. Similarly, tissue or liquid distant from the focal area may be monitored for unexpected rise, lack of rise or decrease of temperature which may indicate dysfunction or disease, such as vesicoureteral reflux, gastroesophageal reflux, or a number of other diseases.

For example, one or more focused antennas disposed in communication with one or more antennas in communication with radiometers may be positioned on the body of an individual to monitor the temperature change of tissue and/or fluid at a desired depth within the body, such as for detecting fluid temperature in the bladder or some other organ. In some embodiments, focused antennas be placed such that a change in temperature in the kidneys due to reflux of heated urine from the bladder may also be monitored and thus determined non-invasively. This enables a physician to determine that there is vesicoureteral reflux, gastroesophageal reflux, etc., without having to use a catheter or other invasive procedure and potentially traumatize the individual.

Some embodiments of the present invention may include a chair or seat configured to be used with heating and monitoring systems that provide a secure and comfortable resting position for an individual being diagnosed or treated. In some embodiments, the seat may include portions of the array or monitoring devices, and may further be shielded to prevent or reduce microwave energy from reaching undesired areas. In some embodiments, the seat may be in the general form of a child car seat, with restraints and other features generally known to children. The seat may be positioned on or next to a cabinet containing equipment for use with the system, such as a computer and focused microwave antennas Likewise, the seat or seat can be configured for an adult with the heating and monitoring systems being removably attached or built in.

In some embodiments of the invention, garments for wearing by the individual being tested may be formed similar to a diaper or other garment and configured to hold a heating array against the individual and in proper position. Similarly, the garment may be configured to work integrally with the system to provide for comfort and safety during any procedure. For procedures involving the bladder, the garment may be configured as a diaper (or adult undergarment) with an absorbent layer, since testing urinary reflux requires the individual being tested to attempt to evacuate the bladder and urinate. In some embodiments, the garment may include positioning aids to assist in properly positioning the garment on the individual. The garment may also include shielding material to reduce unwanted escape or transmission of microwave energy to unwanted locations.

These and other aspects of the embodiments of a heating and monitoring device are shown and described in the following figures and related description.

BRIEF DESCRIPTION OF THE DRAWINGS

Various embodiments and features of heating and monitoring devices are shown and described in reference to the following numbered drawings.

It will be appreciated that the drawings are illustrative and not limiting of the scope of the invention which is defined by the appended claims. The embodiments shown accomplish various aspects of the invention. It is appreciated that it is not possible to clearly show each element and aspect of an invention in a single figure, and as such, multiple figures are presented to separately illustrate the various details of embodiments of heating and monitoring devices in greater clarity. Several aspects from different figures may be used in accordance with the heating and monitoring devices in a single structure. Similarly, not every embodiment need accomplish all advantages of various embodiments of heating and monitoring systems.

DETAILED DESCRIPTION

Embodiments of heating and monitoring devices and associated methods as shown in the accompanying drawings, which include reference numerals referred to below, provide details for understanding and practice by one skilled in the art. The drawings and descriptions are exemplary of various aspects of heating and monitoring systems and associated methods and are not intended to narrow the scope of the appended claims.

Figure 1:
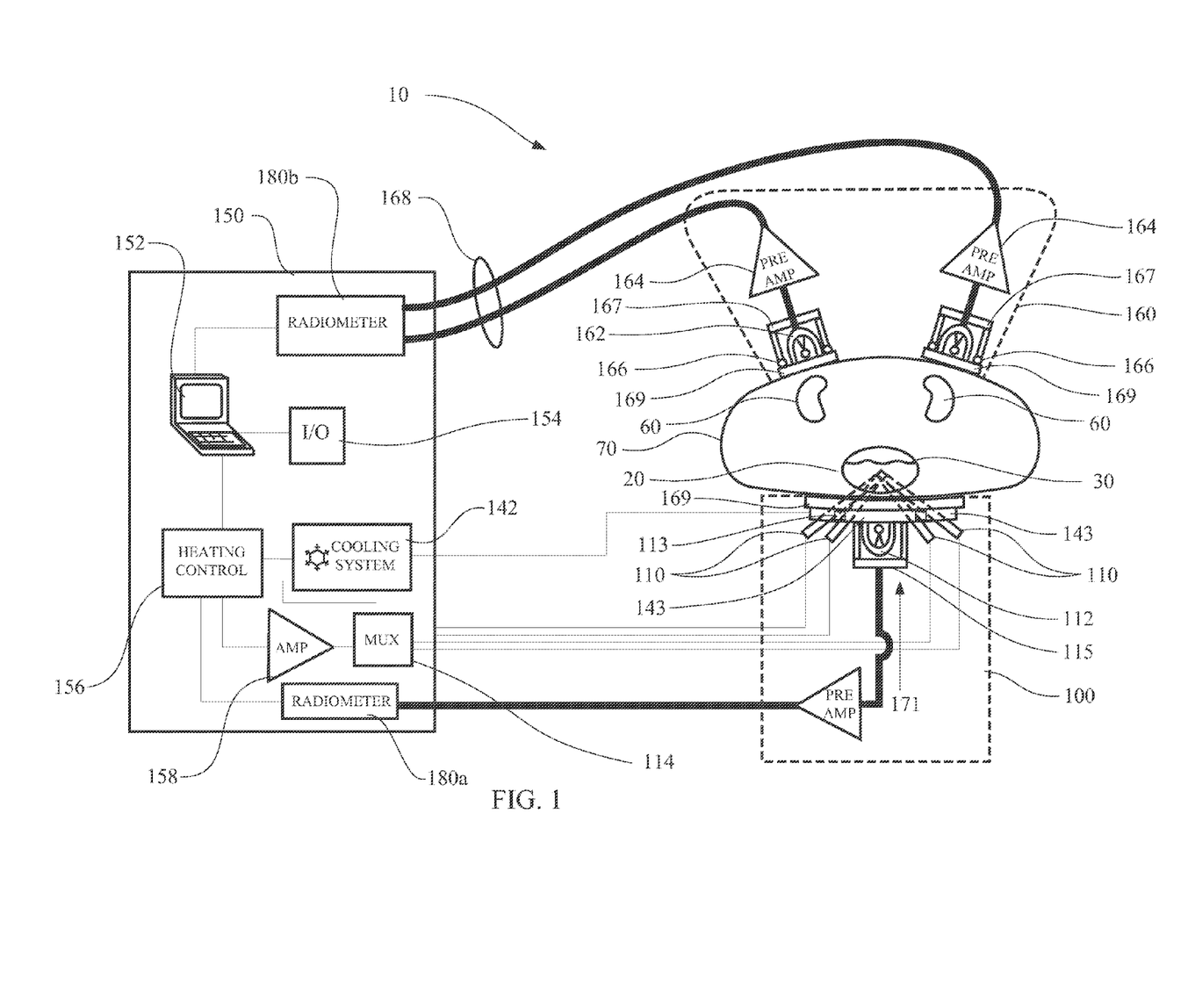
FIG. 1 is a schematic view of an emitted energy heating and monitoring system.

Turning now specifically to FIG. 1, a schematic representation of non-invasive energy emitting heating and monitoring system 10 is shown. System 10 is shown being used to diagnose a potential abnormal condition on a body 70 by applying heat to a bladder 20 filled with urine 30 to see if the urine flows back to the body's kidneys 60. The system 10 typically includes a heating assembly 100, a control assembly 150, and a monitoring assembly 160.

The heating assembly 100 typically includes microwave elements 110, 112. As will be explained in additional detail below, the microwave elements 110 and/or 112 can be used to heat tissue or fluid and can be used to determine the temperature of those tissues. The microwave elements 110 and 112 may be attached to a substrate 120, and may also include a cooling element 143 and/or cooling system 142 which is designed to cool tissue at or near the surface while deeper tissue is being heated by the heating assembly 100.

Microwave elements 110 may be directional microwave emitters, commonly known as antennas, and may be configured to supply energy to a specific area in a body 70. For example, microwave elements 110 may be configured to provide microwave energy directionally into a bladder 20 filled with urine 30 so as to heat the urine. Likewise, the microwave elements 110 can be used to heat fluid in other body tissues.

It should be recognized that while much of the discussion about an individual may be related to an adult human, the term individual should be read broadly to include children and animals.

To protect against burning or discomfort, temperature sensors 113 may be provided in the heating assembly 100 for detecting temperature at or near the surface of the individual's body 70. If the sensors 113 detect excess heat, an alarm may be provided, or the heating protocol adjusted to address the situation. Different adjustments are discussed below in additional detail. (It will be appreciated that the heating assembly 100 and the monitoring assembly 160 may be a single unit in certain applications.

As the microwave elements 110 are used to heat the target area, it is important to monitor temperature in the target area to prevent overheating. This can be accomplished by the heating assembly using one or more of the microwave elements 110, 112 to detect signals from the target area which are then passed to a radiometer 180a which indicates the temperature in the target area. While it is possible to use active microwave elements 110 after they have been turned off, it is presently preferred to use passive microwave element 112 to detect the temperature in conjunction with the radiometer 180a.

Likewise, in certain applications, temperature sensors (e.g. focused antennas) in the monitoring assembly 160 can be use to detect temperature of the target location being heated and/or to detect the temperature in a remote locations, such as the kidneys 60, to ensure that excess heat is not provided, and to gather data used to diagnose an abnormal condition. Thus, for example, focused antenna(s) 162 in the monitoring assembly 160 may collect signals and communicate with one or more radiometers 180b to indicate the temperature at or adjacent kidneys 60.

A control assembly 150 may monitor the system 10 for safety, record the observed results and display the results to the system 10 operator. Thus, the operator may simultaneously monitor the application of heat to (or creation of heat within) one part of the body 70 and detect changes in heat at a second location.

In the heating assembly 100, microwave elements 110 may be placed in an array, and may be arranged and/or spaced apart from each other in the array such that microwave elements 110 provide for a convergence point or area, such that focal area 116 may be affected by the aggregate energy of each of microwave elements 110. Since each of microwave elements 110 may be directional, the energy emitted by microwave elements 110 may travel through body 70 in a generally columnar application. Microwave elements 110 may be arranged in an array in such a way that the convergence of each of microwave elements 110 occurs principally or entirely in the interior space of bladder 20, heating urine 30. This may be accomplished by placing the microwave elements 110 on a flexible substrate 120 or by use of a rigid substrate which can have connections (i.e. pivot attachments) which allow the microwave elements 110 to be angled to adjust for the depth of the target. (For example, a bladder on an overweight adult will be much deeper than a bladder on a thin child). Alternatively, the heating assembly 100 could be preconfigured for various depths of target tissue, with the physician selecting the assembly which is most appropriate for a particular individual.

In some embodiments, anatomy may be consistent enough to allow a holder to naturally direct microwave elements to the target tissue based on placement on the skin. In one embodiment, the physician selects a heating assembly that conforms to the surface of the individual. When placed on the skin using the individual's anatomy as a guide, the microwave elements naturally focus to a target tissue. The holder may include pivot attachments that may have markings that allow the microwave elements to be adjusted based on specific characteristics of the individual such as height, weight, and/or girth.

Generally, each of the columnar energy emissions heats all tissue or fluids within the columnar area. Thus, focal area 116 will receive an aggregate of the combined energies of the overlapping columnar energy emission areas for that area, increasing the energy absorption and subsequent heating of urine 30 within bladder 20. With four microwave elements 110 as shown in the embodiment illustrated in FIG. 2, the amount of energy applied to the surface of body 70 and other tissues and fluids outside of the targeted focal area 116 may be reduced from that of a single microwave element 110, spreading out the energy over a larger surface area and volume of tissue while not diminishing the energy absorbed in focal area 116. For example, in an array with four microwave elements 110, the skin of body 70 located directly under microwave element 110 will typically receive less energy than would have been required to heat urine 30 with only a single microwave element 110.

In some embodiments, microwave elements 110 may be designed such that each microwave element 110 emits a generally columnar energy emission. In some embodiments, the dimensions of the columnar energy emission may be selected to maximize the profile of focal area 116 while minimizing excess heating of surrounding tissues. The columnar shape or lobes of the radiated energy may be of any configuration desired by a practitioner to provide energy to a focal area 116.

The energy from microwave elements 110 may be additive when supplied to and absorbed by focal area 116. For example, the energy from each of the overlapping focal planes contributes to the energy received by the focal area 116. Adjusting the overlapping focal planes may maximize the energy applied to focal area 116, while minimizing the energy applied to tissues outside of focal area 116. Based on the geometry of the array of microwave elements 110 on heating assembly 100, the energy emitted from the array may be further maximized by adjusting transmission times, direction, frequency, and amplitude of the energy emitted.

For example, in some applications a first microwave element 110 could emit a high energy emission for a few seconds and then cease. The microwave element 112 could quickly monitor the temperature of the bladder 20 and then a second microwave element could emit a high energy emission for a few seconds, followed by additional monitoring of the temperature of the bladder 20. The process is repeated until the bladder has reached a desired temperature. However, the tissue between the bladder and any given microwave element 110 would heat much less than if a single heating element were used. Moreover, blood passing through nontarget tissues would tend to conduct heat away from said tissues, while the liquid in the bladder would tend to retain the heat. Between alternating application of energy and the conductive cooling, the heating in the bladder will be significantly greater than the other tissues.

In other applications, each of the microwave elements 110 (whether it be four or a different number) could be activated in sequence and then the microwave element 112 and radiometer 180a used to check the temperature of the target. By applying energy from multiple locations, the heating of tissue other than the target tissue is reduced, lessening the likelihood of burns or discomfort.

Providing a plurality of different application protocols is desirable because different tissues or other intervening structures have different reactions to microwave energy. According to our experience, tissues with higher salt content will absorb more microwave energy than lower salt content tissues. The bladder and muscle tissue have been observed to absorb more energy than fat tissue. Vascular tissues, such as muscle tissue, appear to cool faster than non-vascular tissue or static liquids, such as the bladder.

Taking advantage of this experience, the microwave elements 110 may be activated in different ways depending on factors such as intervening tissue and focal area. For example, when the intervening tissue and structures may be vascular and/or less responsive to microwave energy, a higher power, multiple element simultaneous activation and/or longer duration may be used because of the ability of the tissue to cool and/or absorb less energy. Similarly, if the focal area 116 is within a static liquid with a higher salt content, a higher power, multiple element simultaneous activation and/or longer duration may be used due to the likely better heating of the tissue and/or structure.

In other situations it may be advantageous to use lower power, alternating microwave element activation and/or shorter duration. In some cases, it may be advantageous to mix the activation, duration and power settings. For example, in one embodiment, when heating urine, multiple microwave elements may be activated for a short duration with longer periods for conductive cooling.

For example, in one embodiment with four antennas numbered A, B, C and D, the process of heating urine may be the following. Antennas A and C are activated for a short time at high power. The antennas are de-activated and the radiometer readings are examined. If a higher temperature is desired, antennas B and D are activated for a short time at moderate power or high power depending on the sensed temperature. The radiometer readings are then consulted again. If more power is desired, then the process repeats with A and C again.

The process allows the intervening tissue of A and C to cool during the radiometer readings and B and D's activation. Furthermore, it aids in preventing noise during the temperature reading from the passive element 112 and radiometer 180a, as the radiometer may be detecting a small signal that may be on the order of −160 dBm.

In some embodiments, the attitude of each microwave elements 110 relative to each other may be fixed such that the location of the focal area is known based on the physical configuration of heating assembly 100. Similarly, in some embodiments, substrate 120 may be rigid to provide structure to allow fixed relative positioning of microwave elements 110. In other embodiments, rigid microwave elements may be placed on a flexible structure that is carefully placed and may be adhered to the individual. The placement on the body acts as the fixed relative positioning of the microwave elements.

Microwave element 112 may be a passive antenna for monitoring temperatures of portions of body 70. For example, microwave element 112 may be a passive element for measuring the condition, including temperature, specific heat, rate of heat dissipation, etc., of the focus point or focal area. In some embodiments, microwave elements 110 may be used to both emit microwave energy when active, and passively to monitor conditions of tissue, such as temperature, when not emitting energy (although such would be more difficult than using a passive element for such monitoring). In such embodiments, microwave element 112 may not be necessary. Similarly, in some embodiments, microwave element 112 may be replaced with a focused antenna similar to those in the monitoring system 160 which are in communication with radiometer 180b.

However, in deeper tissue sensing, it may be more advantageous to have a dedicated sensing antenna as the passive antenna. For example, the temperature signal strength from heated urine may be as small as −160 dBm. Thus, increasing the signal to noise ratio may be advantageous.

Noise may be reduced by methods including shielding and reducing active interference. The passive antenna/element 112 may be provided with a shield 115 so that detection only occurs in the direction of a target area of the body. Any cable connections between the antenna/element 112 and the receiver, such as radiometer 180a, may be shielded to reduce noise. Active microwave elements 110 may be shielded (i.e. shield 117, FIG. 3) to provide directionality to the focal area while reducing or eliminating other directionality. Active interference may be reduced by causing the active microwave elements 110 to cease transmitting during a window of time that sensing may occur (a.k.a. a sensing window). Further active interference may be reduced by causing portions of the control equipment to shut down during a sensing window. In some cases, it may be advantageous to combine the radiometer 180a and passive antenna/element 112 into a single unit that may be placed on the individual. Such a unit may contain one or more of the following a focused antenna, radiometer, output to a computer, a shielding enclosure and an analog to digital converter.

Impedance matching of the radiometer 180a to the body may also be important in signal quality. The impedance may be matched through the fixture 121 (FIG. 3) (i.e. strap or other retention mechanism) to which the antenna is attached. For example, the fixture 121 may use a foam pad to not only conform to the skin's shape, but also impedance match the radiometer to the body. One or more of the passive antenna fixtures may be different than the microwave antenna array fixture, as they may be directed at different anatomy.

In some embodiments, temperature sensors 132 may be used to monitor the surface temperature of body 70 in specific locations, or may be used to monitor the temperature of a cooling system 142. For example, in some embodiments temperature sensors 132 may be placed adjacent to each microwave element 110, as well as in other areas, to monitor surface temperatures of body 70, and in cooperation with control assembly 150, to reduce the possibility of tissue damage or surface burns. Temperature sensors 132 may be any type of temperature sensor configurable to send electronic signals, such as thermistors, thermocouples, or any other suitable devices.

Control assembly 150 may include PC 152 (or other microcontroller, control system, etc.), heating control 156, amplifier 158 and multiplexer 114 (for controlling heating assembly 100), cooling system controller 142, and radiometers 180a and 180b. I/O devices 154 may be provided for user interaction and input with system 10. Heating control 156, amplifier 158, and multiplexer 114 may be used, along with PC 152, to control the output of microwave elements 110.

In some embodiments, microwave elements 110 may be activated and deactivated in a pattern or sequence to limit potential damage to body 70, while obtaining the desired heating of an internal organ or tissue. Microwave elements 110 may be activated and de-activated simultaneously, or may be selectively activated and deactivated individually and/or concurrently with one or more other microwave elements 110 in a pattern. The power, duration, and sequence of activation of microwave elements may be controlled by heating control 156. The control may further be refined based on measured surface temperatures of body 70, temperatures of cooling elements 143, or based on any other desired input or parameter such as a pre-determined energy output profiles or individual physiology and anatomy. Thus, heating control may depend on such factors as body fat content, bladder size/fullness and the size of the individual.

For example, when heating urine, multiple microwave elements may be activated simultaneously for a short duration at a desired energy level (low, medium or high) followed by an inactive refractory period. Blood flow from vascular tissues, such as muscle, rid the intervening tissue of excess heat. Since the bladder does not have a similar blood flow, the urine will stay heated.

In some embodiments, amplifier 158 may provide microwave energy to microwave elements 110 through multiplexor 114 or from individual amplifiers. Preferably, the energy is in the microwave ISM bands, with a preferred frequency range of 902 MHz to 928 MHz with a preferred frequency of 915 MHz. However, other models outside the U.S. may need to use alternate ISM bands. Therefore a frequency range of 863 MHz to 870 MHz may also be desirable in other countries, such as those in Europe. The microwave energy supplied by amplifier 158 may be about 100 W at about 915 MHz. Each of microwave emitters 110 may be capable of emitting the entire output of amplifier 158, or some portion thereof.

In contrast, the energy received by a sensor such as the radiometer 180a or 180b may be between about 1-4 GHz. In fact, the energy emitted by the body 70 is believed to correspond to an integral of the heat of all the tissue to the detected depth. The detected depth is believed to depend on the frequency selected. Thus a measurement at two different frequencies may correspond to a heated volume. The heated volume may then correspond to a temperature at the heated volume. Thus, a multi-frequency radiometer or two or more radiometers may be used to detect and/or quantify temperature at a depth in a non-invasive way by comparing first and second energy levels. Another benefit of multi-frequency radiometers is that depth may be adjusted on a per individual basis. In some embodiments, the frequency emitted may more particularly be between about 1.2-1.4 GHz.

These results may then be compared to an actual, normalized or expected energy level. The normalization may be based on anatomical data. In one embodiment, the examined depth may be between 2 cm and 7 cm. In one embodiment, the measured levels are presented by an image. The image may be based on actual values or calculated values, such as a delta between actual and expected values. In some cases, quantifying the data may require integration to determine an aggregate of energy change.

In some embodiments a target of total energy supplied by system 10 to body 70 may be about 5 W to 60 W over about 5-20 min. The amount of energy emitted should be sufficient to heat the targeted body portion to a desired temperature, such as raising the temperature of urine 30 a measurable amount over body temperature. The target temperature may be sufficient such that the heated urine may be detected in the kidneys during a reflux event, but not so hot as to damage tissues or cause significant discomfort. Heating assembly 110 may be connected to control assembly through connector 114.

In some embodiments, cooling system 142, along with cooling element 143, may be used to cool the surface of body 70 at or near where heating assembly 100 supplies energy to body 70. In one embodiment, cooling system 142 may circulate and monitor cooling fluid through cooling element 143. The cooling system 142 may also alternatively actively remove heat from the area using a heat sink, heat pump, heat pipe, or other similar devices alone or in combination, as represented by cooling element 143. Cooling system 142 may provide signals to heating controller 156 indicating the temperature and status of the cooling system and/or surface of body 70, such that the system may maintain a safe operation. In one embodiment, the cooling system is controlled based on signals from the controller.

In some embodiments, system 10 may not have cooling system 142, but only cooling element 143. Cooling element 143 may be a cooling gel, water, or other cooling medium or device. In some embodiments, cooling element 143 may be configured to be replaced intermittently as cooling element 143 is heated by energy emitted from microwave elements 110. In some embodiments, cooling element 143 may be fixedly coupled to substrate 120. Cooling element 143 may be configured to circulate a cooling medium, such as water, or may house, or be formed from a cooling medium, such as a cooling gel.

In one embodiment, a heat sink and heat pipe structure (collectively 143) is embedded in a flexible and disposable fixture. The heat sink collects heat from the body surface and/or the microwave antenna elements. The heat pipe then wicks away the heat from the heat sink. The heat sink and/or heat pipe may have internal temperature sensors to report the current temperature of the system. If used in conjunction with temperature sensors on the skin, the system may be able to determine the effectiveness of the cooling system. Effectiveness of the cooling system may also be a lead indicator of blockages or stoppages of active or passive portions of the system. These problems may include heat sink fin buildup, clogged heat pipes, or lack of sufficient cooling medium (air or water).

Monitoring assembly 160 may include one or more focused antenna 162. Each of focused antennas 162 may have a corresponding signal conditioners including pre-amps 164 and filters and positioner 166. Monitoring assembly 160 may have shielding 167 to shield the focused antennas 162 from the control assembly 150. The shielding may be required to avoid interference and to allow proper calibration and detection by each focused antenna 162. The shielding 167 may be a fabric, mesh, or any other suitable material. Important shielding may include conductive shielding from the active antennas and the individual's skin, thus preventing potentially substantial causes of ambient noise. The shielding 167 may be constructed as part of a disposable fixture, through materials such as conductive foam.

Focused antenna 162 may be positioned to detect changes of temperatures in the body, such as kidneys 60. In some embodiments, multiple antennas 162 may be used to detect temperatures in various locations in each kidney 60, or of each kidney 60, independent of each other. Monitoring assembly 160 may be connected to control assembly 150 by connector 168. Similarly, a focused antenna 162 may be used to monitor the temperature of urine 30 in bladder 20, and may be positioned with, or may be incorporated into heating assembly 100. In some embodiments, the desired depth of measurement within the tissue may be adjusted based on physiological and biometric data, as well as frequency and intensity adjustments.

The frequency may be adjusted based on several different factors. The adjustment may be normalized on typical anatomy measurements. In some embodiments, the adjustment is based on inferred or measured data from other imaging data, such as an ultrasound, MRI, or from prior baseline measurements. In other embodiments, the entire area may be imaged by varying the sensor's detected frequency range.

Radiometer 180b may be provided in control assembly 150, or in monitoring assembly 160, to receive input from focused antennas 162 and provide coherent data to PC 152 corresponding to the input from focused antennas 162. In some embodiments, radiometer may be located in monitoring assembly 160, within the shielding of monitoring assembly 160.

Positioner 166 may be configured to work in conjunction with a fixture of focused antenna 162 to allow a practitioner to direct the focused antenna 162 to detect temperature in a desired location within body 70. A practitioner may locate one or more anatomical features to facilitate desired positioning of focused antenna 162 over tissue, internal body portions and/or fluids at a depth to be monitored, such as a bladder with urine, or a kidney. In some embodiments, a focused antenna may be placed to detect both the temperature of urine in a bladder, and a second focused antenna may be placed to detect the temperature of fluids in a kidney. In some embodiments, the anatomical feature may be detected using ultrasound to ensure proper placement of focused antenna 162. Positioner 166 may then be used to hold focused antenna in place, and may be adjusted as desired. The described methods of positioning of focused antenna 162 may also be used to position heating assembly 100.

Steps to use the device may include: Locating an anatomical feature associated with a first desired internal body portion; positioning a first device based on the locating the anatomical feature, wherein the first device is configured to alter a condition of the first internal body portion; positioning a second device on the individual, wherein the second device is configured to monitor the condition of a second internal body portion; and applying microwave energy from the first device to the individual, the energy being configured to increase the temperature of the first internal body portion without injuring the individual. Optional steps may include: further comprising monitoring the condition of the second internal body portion; further comprising locating a second anatomical feature associated with the second desired internal body portion, wherein the positioning the second device is based on the locating an anatomical features associated with the second desired internal body portion; or using an ultrasound device to locate the anatomical feature.

Figure 4:
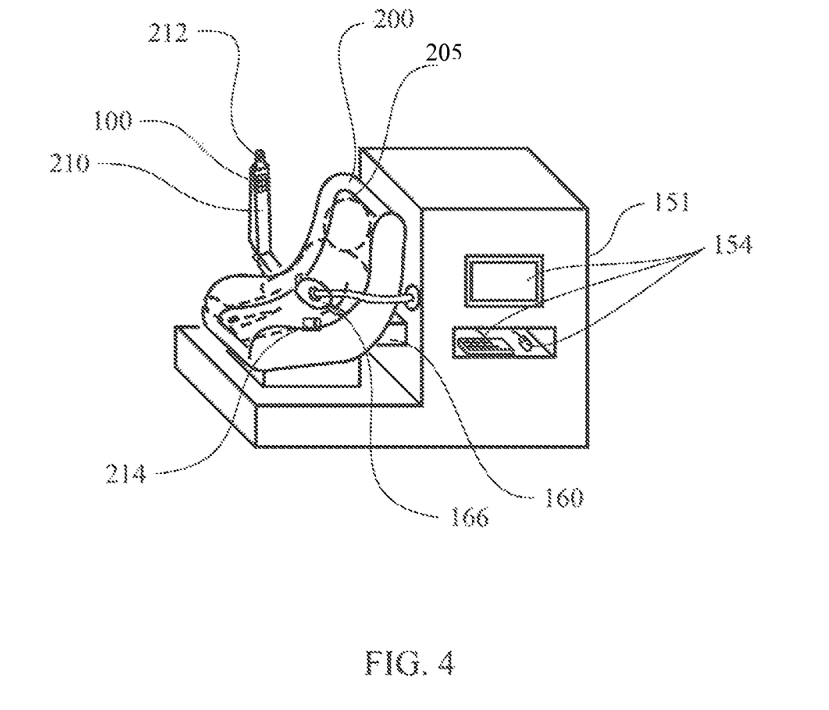
FIG. 4 is a functional representation of an emitted energy heating and monitoring system.

In some embodiments, positioner 166 may be coupled to a seat 200, such as is shown in FIG. 4, in an area located proximate to the portion of a individual 205 to be monitored. Positioners 166 may provide for multi-axis positioning of focused antenna 162, to allow a practitioner maximum allowance to properly position focused antenna 162 with respect to a targeted point or region, such as a desired portion of a kidney. For example, positioners 166 may be coupled to seat 200 such that the attachment allows for adjustment laterally, vertically, and axially of focused antenna 162.

In some embodiments, positioner 166 may be disposable. For example, a disposable contact member with positioners 166 may be provided to directly contact body 70, allowing monitoring assembly 160 to be attached in the appropriate location relative to body 70, while allowing for the disposable contact member to be thrown away after each use, or when soiled by a individual being treated with system 10. For example, positioner 166 may include an adhesive portion for temporarily affixing positioner 166 to an individual being treated.

In some embodiments, positioner 166 may include an impedance matching element 169 placed between focused antenna 162 and the individual being treated. The impedance matching element 169 may be selected based on measured biological data from the individual to allow focused antenna to be tuned for each individual being treated. The impedance matching element may be formed from plastic, or other suitable material, and may be physically designed to provide a desired impedance matching effect, such as thickness, density, etc. In some embodiments, the impedance matching element may be formed such that it may be affixed to the individual being treated or diagnosed and may be used as a positioning aid to help place focused antenna 162 in correct position relative to the physiology of the individual being treated.

In another embodiment, a fixture 121 may be adhesively applied to the body 70. With reasonable placement, normal contours of the body may direct the focused antenna 162 to the correct anatomic regions. Conductive foam 169 (i.e. an impedance matching element) may be used around the focused antenna 162 to shield the focused antenna 162 from noise. A dielectric foam may be applied between the antenna and the body to aid in a predictable electrical pathway to the desired target area.

The fixture 121 (FIG. 3) may be configured with a receptacle 171 to accept and release the focused antenna 162 or an assembly containing the focused antenna, such as a combination of antenna and radiometer Likewise the fixture 121 may have receptacle 171 for the passive antenna 112 (which can function as a focused antenna). As the antenna and/or assembly may be expensive, reuse of the assembly may be cost effective. Thus, the disposable portion of the fixture 121 may include the receptacle that directs the focused antenna 162 or passive antenna 112 to the proper target area, while providing shielding.

The rate and magnitude of thermal change may be compared to expected data. The differences may indicate a disease and/or diagnosis as well as a measurement of severity. Further, the data may indicate or provide a factor of indication in the amount and duration of fluid migration between bladder and kidney. Thus with normalized data, the system may include a temperature trigger that may automate a portion of the diagnosis and/or determination of severity.

Measurements by the system of thermal changes may be converted to graphs or other visualizations of the measured data set, including color real-time manipulable 3 dimensional images. The visualizations may grant an operator a quicker understanding of the data. As discussed above, the image data may be based in the integral of the temperature in the direction of the temperature sensor (such as a radiometer). More resolution may be obtained by overlapping sensor detection areas, especially with a different direction. In fact, the image may aid the operator's use and diagnosis in real-time. In some embodiments, the image may be displayed on I/O device 154, as I/O device 154 may be one or more of a monitor, touch screen monitor, or other data entry device keyboard, mouse, or any other I/O device desirable for use with system 10.

In some embodiments, heating controller 156 may be used to control a safety turn-off based on temperatures monitored in or on body 70. Algorithms may be used to limit energy output based on the size and age of the individual, inflated size of the bladder, thickness of muscle and intervening tissue, temperature sensors in the cooling apparatus, any temperature sensors in the bladder and temperature sensors on the skin. For example, if input from temperature sensors 132, passive microwave element 112, focused antennas 162, or other input indicates the possibility or likelihood of injury to body 70 or an anomalous reading, heating controller 156 may shut down the procedure to avoid injury to body 70. Similarly, temperature inputs may be constantly monitored and the output at microwave elements 110 adjusted accordingly to optimize the heating rate and avoid injury or unwanted tissue damage according to anatomy. Such adjustment, safety shutdown and monitoring, may be done automatically by control assembly 150. Adjustments may include: selectively cycling which portion of the focused array emits energy; altering the duration of time the focused array emits energy; altering the period at which at least a portion of the focused array emits energy tuning off the focused array, etc., such that an optimum energy may be emitted without damaging tissue.

In one embodiment, the heating assembly 100 and the monitoring assembly 160 may be wirelessly coupled to the control assembly 150. The wireless coupling may allow the individual more comfort and/or freedom of movement. In some procedures, the individual may be required to urinate the heated liquid. With wireless coupling, the individual may be able to use a normal restroom while being diagnosed.

With remote monitoring, the system may require more hardware that is respectful of the equipment. For instance, the wireless communication may need to cease during the detection phase of a radiometer to reduce interference. Thus, the system may need local storage to store and forward the results after the measurements. Procedures may also have different power requirements. Thus a lower power procedure may use a small portable power supply, such as a battery or fuel cell, that may strap on the individual. Higher power procedures may require a power supply that is separately wheeled by the individual or an attendant.

Figure 2:
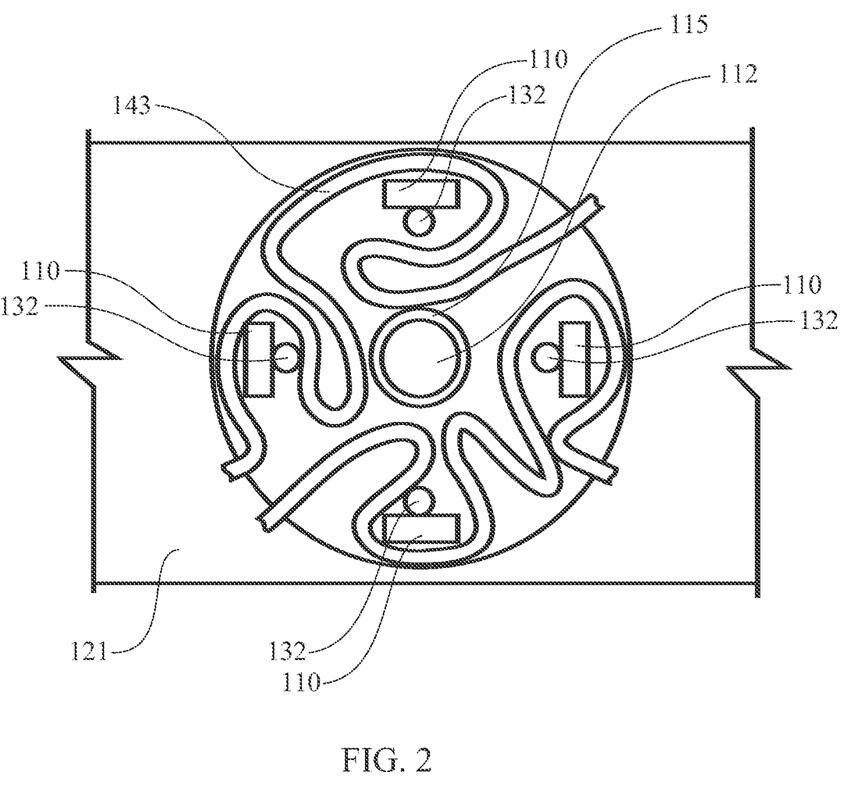
FIG. 2 is a schematic view of an emitted energy heating and monitoring device.

Turning now to FIG. 2, a schematic view of an emitted energy heating and monitoring device is shown. The array may have two or more of microwave elements 110. FIG. 2 illustrates four microwave elements 110. It will be appreciated that as many microwave elements 110 as desired may be used in the array on heating assembly 100. In some embodiments, microwave elements 110 may be lobes of a single microwave antenna, generating separate energy emissions from each lobe such that the lobes work in a manner similar to distinct microwave elements 110 as described below.

The heating assembly may include rigid microwave elements 110 on a flexible, disposable fixture 121 such as a band, strap or other retention mechanism. The fixture 121 may contain or use a layer, such as a dielectric foam, allowing the microwave antenna a more predictable electrical pathway to the focal area. The system may also be shielded to prevent the scattering of microwaves to the back or side of the assembly. This shielding may be accomplished through a backplane, more conductive foam or other shielding methods.

Figure 3:
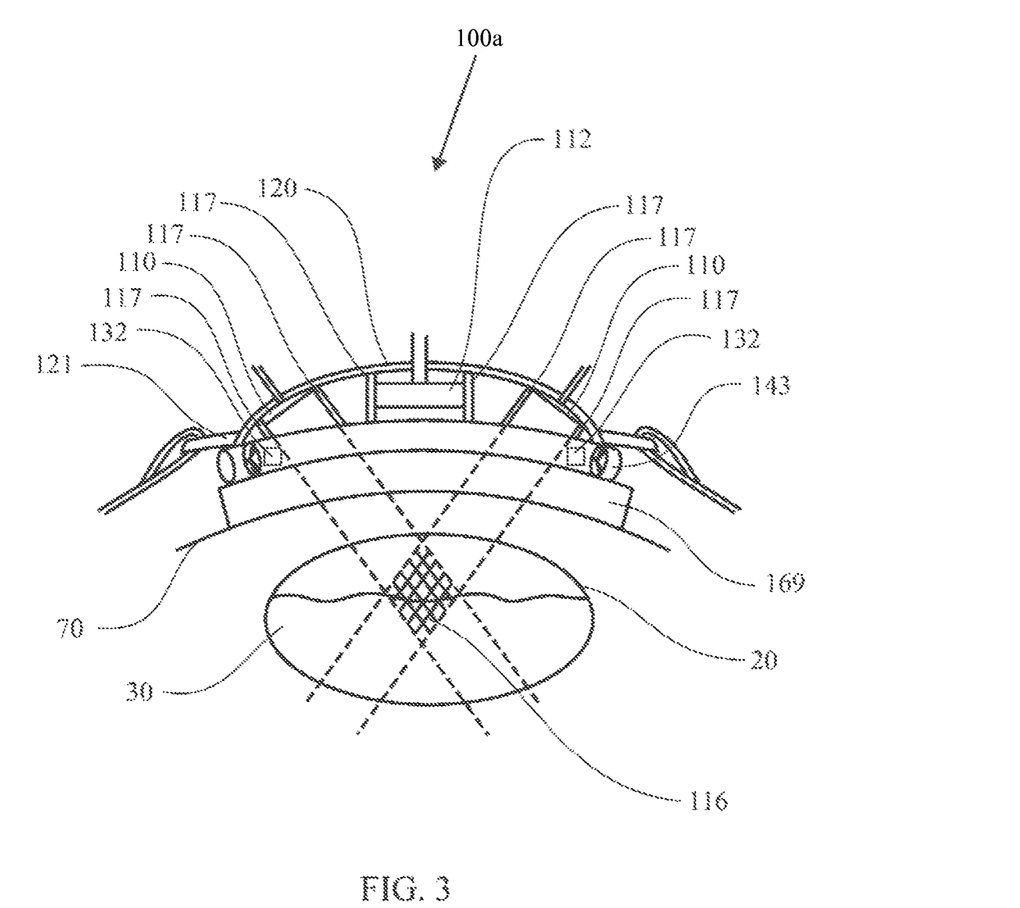
FIG. 3 is a cross sectional view of an emitted energy heating and monitoring device in use on a individual.

Turning now to FIG. 3, a cross sectional view of an emitted energy heating and monitoring device 100a in use on an individual is shown. Individual microwave antennas 110 may be directed to a focal area 116, such as urine in a individual's bladder. A cooling element 143 may be used to reduce the temperature of the skin as raised by the microwave antennas. A passive antenna 112 (or focused antenna) may be used to monitor the temperature at the focal area 116 and/or a target area for diagnosis.

Thus, the heating and monitoring device 100a, may form the heating assembly 100 and be used in conjunction with the monitoring assembly 160, or may be used for both functions in appropriate circumstances, i.e. determining temperature change in a relatively small area.

Turning now to FIG. 4, a seat 200 may be provided on a cabinet or base 151 housing a control system 150. Similarly, monitoring system 160 may be directly coupled to seat 200. Heating assembly 100 may be provided as a portion of seat 200, or as a device configured to be coupled to seat 200. For example, seat 200 may be similar to a car seat familiar to a child, or may be a full-sized seat configured for receiving an adult. In some embodiments, chair or seat 200 may include a formed portion and a soft portion covering part of the formed portion to provide a comfortable seating surface for individual 205. In some embodiments, seat 200 or portion thereof, may be formed or molded from a microwave resistant plastic.

Heating assembly 100 may be coupled to a restraint portion 210, such as a lap belt, chest belt, restraint arm or other structure configured to be positioned across a portion of the individual 205. The heating assembly 100 and the monitoring system 160 may be fixedly attached to the seat, or may be removable, to allow for different configurations depending on the particular anatomy of the individual which is the focus of testing. For example, the monitoring assembly may be slidable along the seat due to a plurality of slots, etc. so as to accommodate different sized individuals.

In another embodiment, all or part of the heating assembly 100 is separate from the seat 200 and restraint portion or lap band 210 and may even be disposable. Restraint portion 210 may include fasteners 212 and 214, including a latch and latch receiver, for releasably securing restraint portion 210 to seat 200. In some embodiments, positioners 166 may be positioned to provide contact between focused antennas 162 and individual 205.

Monitoring assembly 160 may be removably, or permanently coupled to seat 200. Shielding of monitoring assembly 160 may be incorporated into seat 200 and into restraint portion 210, where a shielded focused antenna similar to those in monitoring assembly 160 may be used. An impedance matching foam may be attached to the seat such that it forms an impedance matching layer between the monitoring assembly and the individual. The foam may also be made disposable, such that the foam may be thrown away, resulting in a reduced cost of sanitizing the seat and sensors.

It will be appreciated that the relative position of the heating and monitoring assemblies 100 and 160 will depend on the structures to be heated and monitored. Thus, it is conceivable that for certain diagnostic procedures, the heating assembly may be attached to the seat 200 and the monitoring assembly may be held to the individual by a lap band, shoulder band, etc. Thus, the shielding and movability of the heating assembly 100 and monitoring assembly 160 may be reversed.

In one embodiment, the seat may be coupled with an entertainment system. Thus the individual may be entertained and relax while a procedure as described in this disclosure is performed. The entertainment system may include sound and/or video equipment. In one situation, the equipment may also contain a two-way communications system, such that the individual may page or otherwise get the attention of health care staff or the staff may converse with the individual from a distance.

Figure 5A:
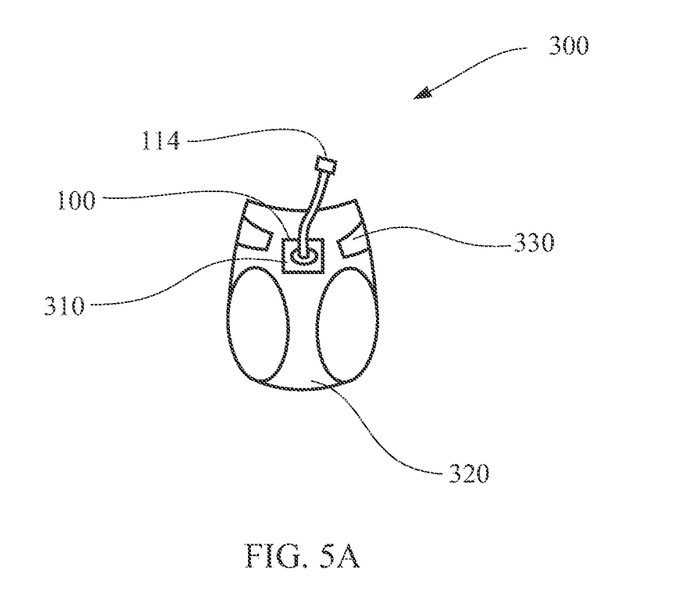
FIG. 5A is a functional representation of an exemplary heating and monitoring device holder in the form of an undergarment.
Figure 5B:
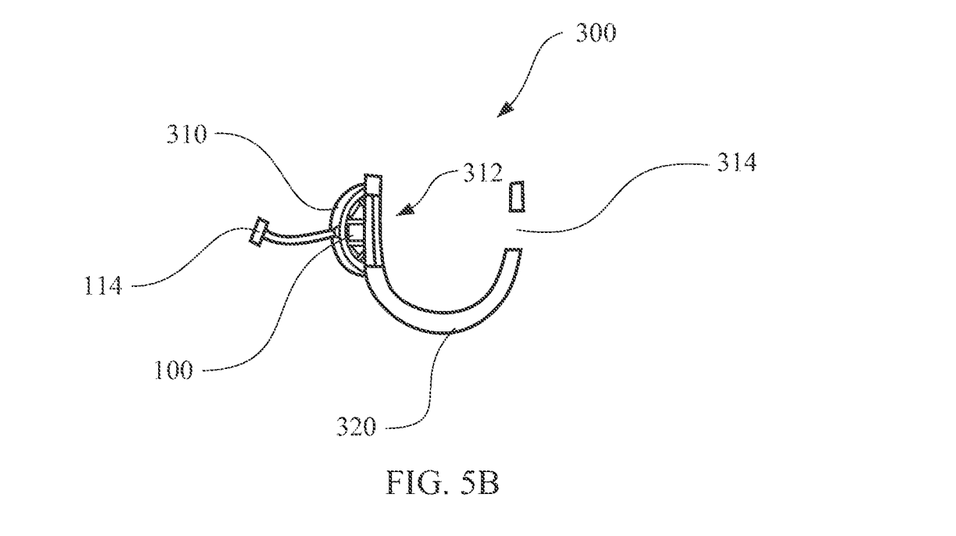
FIG. 5B is a cross sectional view of the device holder in FIG. 5A.

FIGS. 5A and 5B show an alternate configuration of the present invention in which heating assembly 100 may be provided in holder such as a garment 300, which may be a disposable diaper for an infant or an undergarment for wearing by an adult. In other embodiments, heating assembly 100 may be readily attachable to a disposable diaper, or may be otherwise provided in a package comfortable for an individual.

In some embodiments, portions of heating assembly 100 may be included in a disposable diaper, with others may be included in a restraint portion of seat 200 similar to that shown in FIG. 4. In some embodiments, seat 200 and other accompanying elements may be constructed to resist the microwave energy and to limit or eliminate unwanted microwave energy from being transmitted to the area around seat 200 or system 10.

Garment 300 may include coupling portion 310 with an interface, such as a pocket, which may allow for attaching at least a portion of heating assembly 100 to garment 300. In some embodiments, garment 300 may include open area 312 to allow heating assembly 100 to contact the individual directly. Garment 300 may also include securement portion 330 for attaching garment 300 to the individual. For example, securement portion 330 may be tabs that secure portions of garment 300 to itself. Securement portion 330 may be adjustable to allow garment 300 to be adjusted to allow heating assembly 100 to be located properly on the individual depending on the individual's size. Garment 300 may include absorbent material 320, similar to a standard diaper or incontinence undergarment. Since reflux generally occurs when a individual attempts to urinate, having a disposable absorbent material 320 like in a diaper helps to facilitate comfort during procedures. In some embodiments, garment 300 may also include cooling element 143, either integrally formed in garment 300, or attached or otherwise inserted into garment 300. In some embodiments, garment 300 may be disposable, with portions of heating assembly 100 manufactured into garments 300, and disposable after each use. In some embodiments, garments 300 may include access 314 for a focused antenna 112, as discussed above, for separate installation. Similarly, in some embodiments, portions of garment 300, such as absorbent material 320 may include shielding materials to help improve the sensitivity of the various monitoring devices in system 10.

Figure 6:
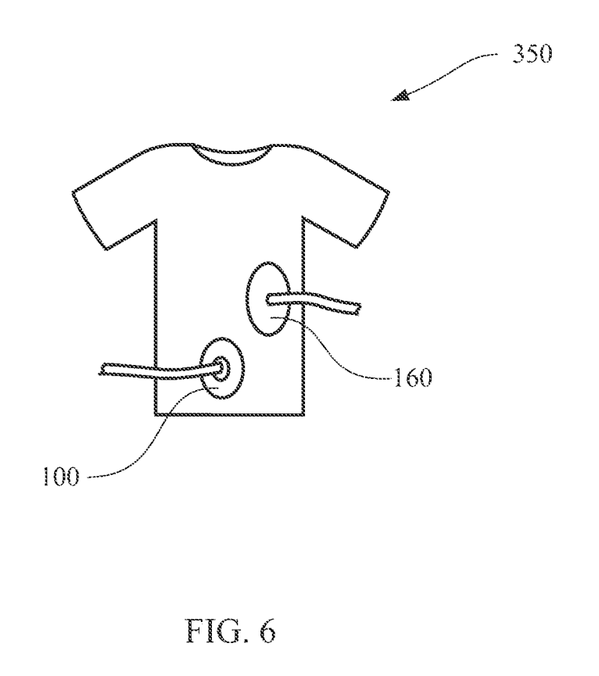
FIG. 6 is a cross-sectional view of an alternate garment having a heating system and monitoring system formed therein.

Turning now to FIG. 6, there is shown an alternate embodiment of a holder or garment 350 in accordance with the principles of the present invention. The garment 350 may be worn by a individual. The garment 350 has the heating assembly 100 and the monitoring assembly 160 attached thereto. All or part of the heating assembly 100 and/or the monitoring assembly 160 may be discarded with the garment 350. However, due to the cost of the focused antennas and radiometer assemblies, it is presently preferred to have at least those structures be removeably attached to the garment 350 for reuse with further procedures.

Although system 10 has been described with microwave elements 110, other heating methods may be provided and used with other portions of system 10. Similarly, the components of system 10 may be provided in any number of configurations, and not necessarily in the particular configurations and locations illustrated in the Figures. For example, multiplexor 114 may be located on substrate 120 of heating assembly 100, or PC 152 may be remote from the rest of system 10, being connected wirelessly to other components of system 10. Other configurations and uses, either individually or with one or more other components taught in the Figures, are contemplated by this application.

While the present invention has been discussed primarily with respect to vesicoureteral reflux, there are numerous other scenarios in which the principles of the present invention could be used. For example, systems and methods in accordance with the present invention can be used regarding the nervous system.

There is not a current imaging method that adequately shows flow of the cerebral spinal fluid through the aqueducts to and from the spinal column. Current studies simply show dilatation of obstructed chambers. Warming either the spine or the head and measuring the temperature in the opposite end (or some other location) of the nervous system would easily show the migration of the warm cerebral spinal fluid through its proper ductal network. This flow could be timed to know how rapid this occurs and whether any abnormalities exist.

Likewise, the present invention could be used in the dental field. Applications for the system and methods of the present invention may be as simple as having the patient drink a warm drink or a cold drink and measuring how rapidly the teeth returns a normal temperature, indicating good blood flow and viability of the teeth. Sensitivity to hot or cold is a common problem and difficult to determine exactly which tooth is causing the problem. The systems and methods of the present invention, with their ability to determine actual temperatures may be very helpful in determining the underlying condition.

Likewise, the present invention could be used in the pulmonary field. Anticipated benefits for imaging the pulmonary tree may be significant. Currently there are few diagnostic studies to determine ventilatory patterns deep within the bronchial tree and the alveoli. The patient could be asked to breathe warm or cold air and the systems and methods of the present invention could measure temperature changes throughout the lung fields, determining which areas were easily ventilated and watching their return to normal.

The systems and methods of the present invention could be used as a way to watch the lung disease processes resolve. Once a patient has breathed warm or cold air, the systems and methods of the present invention should be able to observe the normal blood vessels that don't change with the ventilation temperature to determine perfusion in the lungs and ought to be an alternative method to evaluate ventilation and perfusion defects.

The systems and methods of the present invention could also be used in the cardiovascular context. For example, an individual could have the heart warmed and then measurements of peripheral blood flow to any of the following arteries: carotid artery, femoral artery, brachial artery descending aorta, etc. The systems and methods of the present invention could be used to measure peripheral vascular blood flow. Knowing how rapidly the heart was warmed a mathematical calculation of cardiac output could be performed.

As the resolution of the systems and methods of the present invention improves, it may be possible that the coronary vessels could be seen distinctly from the heart chambers themselves, allowing imaging that is currently only available by intravascular catheterizations. Conversely, if a peripheral area, such as a femoral area was warm, we could watch and calculate venous return to the heart, including cardiac output.

The systems and methods of the present invention could be used if the lung fields were warmed, either the right side or the left side, or both sides at once, to observe the vascular tree of the lungs, both pulmonary artery and pulmonary venous systems could be well-delineated.

If an IV was in place an injection of cold bolus of fluid of known amount could be injected and the systems and methods of the present invention could be used to measure the temperature and with thermodilution calculations the cardiac output could be determined accurately.

The systems and methods of the present invention could be used in the genitourinary system (besides vesicoureteral reflux). For example, if the kidney were warm, the urine flowing to the bladder could be seen and measured alleviating the need for an intravenous pyelogram (WP) and at much diminished expense from a CT scan. Warmed bladder urine could be observed during the voiding process and perhaps eliminate the need for voiding cystoureterograms in non-refluxing patients.

On occasions renal cysts are difficult to delineate from a diverticula of the collecting system, which does have a communication with the collecting system. If the fluid pocket was warm and the temperature changes, one could tell it was a diverticulum with the communication to the kidney and if the temperature simply diffused through the kidney, one would know this is a cyst without fluid communication.

Regarding, GI imaging, swallowing warm or cold fluid could be used in conjunction with the systems and methods of the present invention, as the temperature monitoring devices may be used to evaluate esophagus transit and stomach transit times. If the stomach were warm, observation of the esophagus would determine whether there was gastroesophageal reflux. If the stomach were warmed or if warm or cold fluids were swallowed, the intestinal transit time may be calculateable with the systems and methods of the present invention.

Likewise, the traditional barium enema to study the large intestine may still require and catheter and fluid to be placed, but the temperature of the fluid could be adjusted so that the systems and methods of the present invention could be the imaging modality of choice so that no ionizing radiation is required.

Similarly, the flow of bile from the gallbladder, through the bile duct could be imaged by warming the gallbladder and watching the warm bile go down the duct into the duodenum. The systems and methods of the present invention could render such monitoring relatively easy and noninvasive.

In obstetrics and gynecology, the hysterosalpingogram study to determine patency of the fallopian tubes could be done with a cold solution and imaged with the systems and methods of the present invention so that no ionizing radiation would be necessary, especially in the area of the gonads, which can be damaging.

Likewise, during pregnancy, the amniotic fluid could be warmed and the turn over time of the amniotic fluid could be measured, fetal swallowing could be observed and fetal urination would be visible.

In orthopedics, joint spaces have fluid and the fluid could be warmed and observed for even distribution throughout the joint space. This may be a desirable tool for physical therapy for measuring how deep the tissues are being heated and how rapidly the damaged tissue is responding and returning to normal blood flow.

Regarding solid organs, or tissues, scar tissues should warm much differently than normal surrounding tissue because of missed blood flow and over time it would be anticipated that the scar tissue would cool more slowly since there is less blood flow to take the warmth away from the scar. This would help physicians determine whether there was scar tissue or inflammation.

Within inflamed tissue there should be increased blood flow, which should have a different warming characteristic of scar tissue and with the increased blood flow it would be expected that they inflamed tissue would cool faster as the increased blood flow would take the temperature away.

As will be apparent to those skilled in the art in which the invention is addressed, the present invention may be embodied in forms other than those specifically disclosed above without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the example contained in the foregoing description.

What is claimed is:
1. A detector comprising:
 a first radiometer coupled to a first focused antenna configured to determine a temperature of a first portion of a targeted deep tissue structure;
 a second radiometer coupled to a second focused antenna configured to determine a temperature of a second portion of the targeted deep tissue structure;
 a holding mechanism adapted for holding the first and second focused antenna to a skin surface;

an output configured to couple the first and second radiometers to a computer; and a shielding enclosure configured to isolate at least the first focused antenna and second focused antenna from ambient radiation and further configured to provide directionality to direct the first focused antennae to the first portion of the targeted deep tissue structure and the second focused antenna to the second portion of the targeted deep tissue structure.

2. The detector of claim 1, wherein the enclosure further comprises a shielding material.

3. The detector of claim 1; wherein the targeted deep tissue structure comprises a kidney.

4. The detector of claim 3; wherein the portion of a targeted deep tissue structure comprises urine in the kidney.

5. The detector of claim 4; wherein the portion of a targeted deep tissue structure comprises urine in the bladder.

6. The detector of claim 5, wherein the condition comprises the temperature of urine in a bladder.

7. The detector of claim 1, wherein the detector is configured to be coupled to a chair during use.

8. The detector of claim 1, further comprising an analog to digital converter.

9. The detector of claim 1, wherein the targeted deep tissue structure comprises a targeted deep tissue organ.

10. The detector of claim 1, wherein the shielding enclosure is configured to at least reduce receipt of noise signals from a patient's skin tissue.

11. The detector of claim 1, wherein the shielding enclosure is configured to at least reduce receipt of noise signals from deep tissue structures other than the targeted deep tissue structure.

12. The detector of claim 11, wherein the targeted deep tissue structure comprises a targeted deep tissue organ.

13. The detector of claim 1, wherein the shielding enclosure is part of a detachable fixture.

14. The detector of claim 13, wherein the shielding enclosure comprises an impedance matching element.

15. The detector of claim 14, wherein the impedance matching element comprises a conductive foam.

16. The detector of claim 13, wherein the detachable fixture comprises a disposable fixture.

17. The detector of claim 13, wherein the detachable fixture comprises a receptacle configured to receive the first focused antenna and the second focused antenna and to direct the first focused antenna and the second focused antenna towards the first and second portions of the targeted deep tissue structure once the detector has been coupled with the skin surface.

18. The detector of claim 1, wherein the first radiometer is further configured to sense the temperature of the first portion of the targeted deep tissue structure by taking a first measurement at a first electromagnetic frequency.

19. The detector of claim 18, wherein the second radiometer is configured to sense the temperature of the second portion of the targeted deep tissue structure by taking a second measurement at a second electromagnetic frequency.

20. The detector of claim 19, wherein the second electromagnetic frequency is distinct from the first electromagnetic frequency.

* * * * *